United States Patent
Dawson et al.

(10) Patent No.: US 9,157,946 B2
(45) Date of Patent: Oct. 13, 2015

(54) REDUCING MOVEMENT AND ELECTROSTATIC INTERFERENCE IN A NON-RESISTIVE CONTACT SENSOR ASSEMBLY

(71) Applicant: RESCON LTD, Farnborough (GB)

(72) Inventors: Thomas Andrew Dawson, Aldershot (GB); Christian Macedonia, Bethesda, MD (US)

(73) Assignee: RESCON LTD, Farnborough (GB)

( * ) Notice: Subject to any disclaimer, the term of this patent is extended or adjusted under 35 U.S.C. 154(b) by 167 days.

(21) Appl. No.: 13/846,263

(22) Filed: Mar. 18, 2013

(65) Prior Publication Data

US 2014/0152319 A1    Jun. 5, 2014

Related U.S. Application Data

(63) Continuation of application No. 13/834,664, filed on Mar. 15, 2013.

(60) Provisional application No. 61/671,647, filed on Jul. 13, 2012.

(51) Int. Cl.
*G01R 29/12* (2006.01)
*G01R 27/26* (2006.01)
(Continued)

(52) U.S. Cl.
CPC . *G01R 29/12* (2013.01); *A61B 5/04* (2013.01); *A61B 5/6831* (2013.01); *G01R 27/2605* (2013.01); *A61B 2562/0214* (2013.01); *A61B 2562/182* (2013.01)

(58) Field of Classification Search
CPC .......... A61B 5/0408; A61B 5/04; A61B 5/11; A61B 5/0428; A61B 5/6831; A61B 2562/0214; A61B 2562/182; G01R 29/12; G01R 27/2605
USPC .................. 600/372, 382–392; 324/509–628, 324/658–670, 686–688, 691–696, 457; 607/6, 27, 28, 52
See application file for complete search history.

(56) References Cited

U.S. PATENT DOCUMENTS 6,755,795 B2 *  6/2004  Marmaropoulos et al. ... 600/587
6,952,606 B2    10/2005 Anderson et al.
(Continued)

FOREIGN PATENT DOCUMENTS

WO    WO 2008152588 A2 * 12/2008 ........... A61B 5/0428

OTHER PUBLICATIONS

Information Disclosure Statement (IDS) Letter Regarding Common Patent Applications(s), dated Aug. 14, 2014.

*Primary Examiner* — Hoai-An D Nguyen
*Assistant Examiner* — Lee Rodak
(74) *Attorney, Agent, or Firm* — Tillman Wright, PLLC; Chad D. Tillman; Jeremy C. Doerre

(57) ABSTRACT

A non-resistive contact sensor assembly, includes a non-resistive contact sensor device, a first inner region of material in which the sensor device is surrounded or embedded, a boundary region, around the first inner region, that is at least partly comprised of a conducting material and that picks up electrical charge from the first inner region, a second inner region around the boundary region, an outer region around the second inner region, and at least one diode, disposed in the second inner region and connected between the boundary region through the second inner region to the outer region.

20 Claims, 5 Drawing Sheets

(51) Int. Cl.
*A61B 5/04* (2006.01)
*A61B 5/00* (2006.01)

(56) References Cited

U.S. PATENT DOCUMENTS

| | | | |
|---|---|---|---|
| 2004/0073104 A1* | 4/2004 | Brun del Re et al. | 600/372 |
| 2004/0254435 A1* | 12/2004 | Mathews et al. | 600/372 |
| 2005/0054941 A1* | 3/2005 | Ting et al. | 600/529 |
| 2005/0177038 A1* | 8/2005 | Kolpin et al. | 600/372 |
| 2005/0240087 A1* | 10/2005 | Keenan et al. | 600/301 |
| 2005/0275416 A1* | 12/2005 | Hervieux et al. | 324/663 |
| 2006/0064826 A1 | 3/2006 | Kimball | |
| 2006/0247566 A1 | 11/2006 | Gobet et al. | |
| 2007/0192972 A9 | 8/2007 | Kimball | |
| 2009/0254134 A1 | 10/2009 | Nikolov et al. | |
| 2010/0160737 A1 | 6/2010 | Schachar et al. | |
| 2014/0062504 A1 | 3/2014 | Dawson | |
| 2014/0062505 A1 | 3/2014 | Dawson | |
| 2014/0062508 A1 | 3/2014 | Dawson | |
| 2014/0125358 A1 | 5/2014 | Dawson et al. | |

* cited by examiner

REDUCING MOVEMENT AND ELECTROSTATIC INTERFERENCE IN A NON-RESISTIVE CONTACT SENSOR ASSEMBLY

CROSS-REFERENCE TO RELATED APPLICATIONS

The present application is U.S. continuation patent application of, and claims priority under 35 U.S.C. §120 to, U.S. nonprovisional patent application Ser. No. 13/834,664, filed Mar. 15, 2013, which patent application is incorporated by reference herein, and which application is itself a U.S. non-provisional patent application of, and claimed priority under 35 U.S.C. §119(e) to, U.S. provisional patent application Ser. No. 61/671,647 to Dawson, filed Jul. 13, 2012 and entitled "REDUCING MOVEMENT AND ELECTROSTATIC INTERFERENCE IN A NON-RESISTIVE CONTACT SENSOR ASSEMBLY", which '647 application is also incorporated by reference herein in its entirety. Additionally, the entirety of each of the following commonly-assigned U.S. patent applications, and any application publication thereof, is expressly incorporated herein by reference:
(a) U.S. provisional patent application Ser. No. 61/695,986 to Dawson, filed Aug. 31, 2012 and entitled "SIGNAL STABILIZATION IN A NON-RESISTIVE CONTACT SENSOR ASSEMBLY;"
(b) U.S. provisional patent application Ser. No. 61/759,827 to Dawson, filed Feb. 1, 2013 and entitled "SIGNAL STABILIZATION IN A DIELECTRIC SENSOR ASSEMBLY;"
(c) U.S. non-provisional patent application Ser. No. 13/834,918, filed Mar. 15, 2013, and entitled, "SIGNAL STABILIZATION IN A NON-RESISTIVE CONTACT SENSOR ASSEMBLY;" and
(d) U.S. non-provisional patent application Ser. No. 13/835,762, filed Mar. 15, 2013, and entitled, "SIGNAL STABILIZATION IN A DIELECTRIC SENSOR ASSEMBLY."

STATEMENT REGARDING FEDERALLY SPONSORED RESEARCH OR DEVELOPMENT

This invention was made with government support under contract number W911NF-12-C-0004 awarded by DARPA. The government has certain rights in the invention.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

1. Field of the Present Invention

The invention relates to methods that will attenuate or eliminate unwanted movement or electrostatic interference on the signal acquired from non-resistive contact sensors that are used exclusively or in combination with other sensors and the sensor data is utilized for detecting properties of an entity and entities (biological or otherwise). For biological entities the invention utilizes an electric field sensor or sensors for the measurement of the structural and functional characteristics of organs and other structures where the electric field sensor does not have resistive contact with the organism, conferring multiple advantages. More particularly, the invention relates to sensors, sensor housings, fastenings and sensor systems including devices and installations for assemblies for detecting structural and functional signatures associated with electric potentials that may detect a displacement signature within the geomagnetic field, and/or specific components and/or structures that are a component of that entity or entities. Specifically there is no resistive contact between the entity and the signal transduction component of the electric field sensor or sensors. Other sensor types may be added in to provide further information such as for the identification and elimination or attenuation of unwanted electrostatic or movement signal associated with the recording of non-resistive contact electric fields from that entity, in whatever state, such as during active or passive movement.

2. Background

Conventional electrodes act as a current transducer converting ionic currents into electronic ones so electrophysiological status can be assessed. The uses for this are many and broadly range from assessment of neural (EEG), and cardiac (ECG) and skeletal (EMG) muscle activity.

This approach requires conductive contact with the source and has inherent problems. The first of these is the requirement of clean skin exposure. This requirement may compromise continuous usability due to the effects of environmental contaminants, both on the skin and in the atmosphere; extremes of temperature and their resulting general effect on skin due to physiological reactions such as "goose bumps" and excessive sweating as well as other phenomena; and potential reactions to conductive materials. The process of preparing skin and securing a good conductive contact can also decrease compliance, especially in if intended for continuous day to day use. Furthermore, during exercise, the physicality can result in electrodes being displaced. The other issues include: shorting between electrodes, especially when placed in close proximity to each other; and charge transfer which has potential safety implications as well as the issue of the measurement process corrupting the signal.

The problems, outlined above, are solved by the use of capacitive electrodes (non-resistive contact sensors) as they acquire signal through capacitive coupling, not requiring resistive contact with the source. They provide many benefits, including the fact that no electrical contact is required (and so no skin preparation or conducting pads are necessary, and they can be readily moved or relocated to get an optimal signal), they can be miniaturized, they have very low power requirements, and they can be embodied as passive electric field sensors with the result that adjacent sensors do not interfere with each other.

The use of capacitive electrodes for electrophysiological monitoring is not a recent innovation, with Richardson describing it for acquisition of the cardiac signal in 1967 (see *The insulated electrode: a pasteless electrocardiographic technique*. Richardson P C. Proc. Annu Conf. on Engineering in Medicine and Biology 7: 9-15(1967)). This system was, however, flawed being prone to problems including poor signal to noise ratio, voltage drift, electrostatic discharge and parasitic capacitance. These are still problems with capacitive sensor technologies today. Many of those problems have been addressed, at least partially, however problems with electrostatic interference still plague this technology. Electrostatic interference is especially problematic during movement. Movement may lead to a variety of issues that may compromise continuous signal acquisition including: contact electrification between the body surface and the sensor electrode; charge build-up on the body resulting in baseline shift and potential saturation if occurs too rapidly; and movement of the sensor relative to the body that can also lead to baseline shift and saturation (railing).

The use of dry electrodes pressed into direct contact with the person may create triboelectric effects. That is, electrical charges created by sliding friction and pressure. Triboelectric effects of this nature may cause contact electrification where static charges may be delivered to the pick-up electrode. This static charge can produce a near direct current (DC) or very low frequency drift in sensor that may interfere with the physiological alternating current (AC) that is being measured or saturate the sensor causing railing, after which the sensor takes time to return to being able to produce a useful physiologically relevant output. If the electrode moves relative to the body, it will also pick up a geoelectric displacement signal. That is, the effect of the body, an electrically active structure, moving through the geoelectric field that is of the order of 100 $Vm^{-1}$ will cause relative polarization of the sensor that will displace the baseline and may cause the sensor to saturate. An additional source of interference is that of clothing moving on the body. As clothing moves on the body then charge separation can occur when materials that are separated on the triboelectric series donate or receive electrons from each other. After a material becomes charged it may discharge onto the surface of where an electric potential may be being measured thereby interfering with signal acquisition. Cotton is a relative exception to this as it is essentially triboelectrically neutral, or does not accept or give up electrons, so charge separation tends not to occur.

SUMMARY OF THE PRESENT INVENTION

In accordance with one aspect of the invention, a sensor for use with an entity may have a fixed wrapping that is: triboelectrically neutral, such as cotton; triboelectrically matched to the surface being measured, such as leather to skin; or any combination thereof. This aspect of the invention will minimize the likelihood of contact electrification from movement of the dry electrode sensor against the skin.

In accordance with another aspect of the invention, a sensor for use with an entity may be surrounded or embedded in a material that is in full or partial contact with the entity that is: triboelectrically neutral, such as cotton; triboelectrically matched to the surface being measured, such as leather to skin; has conducting components in it that act to dissipate charge to prevent electrostatic build-up; has a compressive or elastic component that pushes the electrode into the surface of the entity to minimize the likelihood of sensor movement relative to the entity; or a combination or permutation of the foregoing. This embodiment of the invention will help minimize the effects of local electrostatic build-up and electrical discharge that may affect the electrode performance, causing drift or saturation.

In accordance with another aspect of the invention diodes may be used for charge transfer away from the sensor.

In accordance with another aspect of the invention the surface region of the entity where a sensor or sensors are housed may be separated from the rest of the surface entity of the entity using a conducting band.

In accordance with another aspect of the invention the sensor may have an electrostatic shield layer, such as a layer of neoprene, over it. On top of this layer may be an additional layer or layers, such as for the dispersion of unwanted electrical charge away from the electrode area to the surface of the entity.

Broadly defined, the present invention according to one aspect is a non-resistive contact sensor assembly, including: a non-resistive contact sensor device, including a dry electrode component; and a cover of anti-triboelectric material in which the sensor device is surrounded or embedded.

In a feature of this aspect, the anti-triboelectric material is a triboelectrically-neutral material. In another feature, the triboelectrically-neutral material is cotton.

In another feature of this aspect, the anti-triboelectric material is triboelectrically-matched to the surface being measured or tested. In another feature, the anti-triboelectric material is leather and is triboelectrically-matched to skin.

In another feature, the non-resistive contact sensor assembly further includes a housing that is treated with an ionized liquid.

Broadly defined, the present invention according to another aspect is a non-resistive contact sensor assembly, including: a non-resistive contact sensor device; an inner region of material in which the sensor device is surrounded or embedded; and an outer region of material; wherein the inner and outer regions mitigate movement of the sensor electrode relative to the surface of the object being measured or tested; and wherein the inner and outer regions create a local area that is relatively protected from the electrostatic build-up and electrical discharge that may otherwise affect sensor performance.

In a feature of this aspect, the outer region includes an elastic material that is bound to, or an extension of, a compressive type wearable article that aids in holding the sensor assembly in place. In further features, the compressive type wearable article is a garment; and/or the elastic material includes elastane and/or natural latex.

In another feature of this aspect, the outer region includes a conducting material that aids in dissipation of charge to the surface of the entity, thereby minimizing the chances that the charge will dissipate in a more localized fashion within the area between the outer region the sensor device.

In another feature of this aspect, the inner region includes a triboelectrically neutral or relatively neutral material.

In another feature of this aspect, the inner region includes an elastic material that acts to hold the sensor device in place, thereby minimizing the likelihood of sensor movement against the object surface and leading, in turn, to less chance of contact electrification and movement artifacts.

In another feature of this aspect, the inner region includes a biasing structure that acts to hold the sensor device in place, thereby minimizing the likelihood of sensor movement against the object surface and leading, in turn, to less chance of contact electrification and movement artifacts. In a further feature, the biasing structure includes a spring.

In another feature of this aspect, the inner region includes material that is relatively triboelectrically matched to the surface of the object being measured, tested, or the like, thereby minimizing the chances that charge separation will occur when this region and the surface of the object may move together.

In another feature of this aspect, inner region includes material that is conductive, allowing for dissipation of any surface or external charge.

In another feature, the non-resistive contact sensor assembly further includes a housing that is treated with an ionized liquid.

Broadly defined, the present invention according to another aspect is a non-resistive contact sensor assembly, including: a non-resistive contact sensor device; a first inner region of material in which the sensor device is surrounded or embedded; a boundary region, around the first inner region, that is at least partly comprised of a conducting material and that picks up electrical charge from the first inner region; a second inner region around the boundary region; an outer region around the second inner region; and at least one diode, disposed in the second inner region and connected between the boundary region through the second inner region to the outer region.

In a feature of this aspect, at least one of the first inner region, the second inner region, and the outer region includes a triboelectrically neutral or relatively neutral material.

In another feature of this aspect, at least one of the first inner region, the second inner region, and the outer region includes an elastic material that acts to hold the sensor device in place, thereby minimizing the likelihood of sensor movement against the object surface and leading, in turn, to less chance of contact electrification and movement artifacts.

In another feature of this aspect, at least one of the first inner region, the second inner region, and the outer region includes a biasing structure that acts to hold the sensor device in place, thereby minimizing the likelihood of sensor movement against the object surface and leading, in turn, to less chance of contact electrification and movement artifacts. In a further feature, the biasing structure includes a spring.

In another feature of this aspect, at least one of the first inner region, the second inner region, and the outer region includes material that is relatively triboelectrically matched to the surface of the object being measured, tested, or the like, thereby minimizing the chances that charge separation will occur when this region and the surface of the object may move together.

In another feature of this aspect, at least one of the first inner region, the second inner region, and the outer region includes material that is conductive, allowing for dissipation of any surface or external charge.

In another feature, the non-resistive contact sensor assembly further includes a housing that is treated with an ionized liquid.

Broadly defined, the present invention according to another aspect is a non-resistive contact sensor assembly, wherein the surface region of the entity where a sensor or sensors are housed may be separated from the rest of the surface of the entity using a conducting band, including: a non-resistive contact sensor device, including a dry electrode component; a first region of material; and a second region of material, wherein at least part of the material is a conducting material; wherein the first region is walled off from the rest of the surface of the entity by the second region.

In a feature of this aspect, the assembly is provided in a wearable form. In another feature, the assembly is provided in the form of a belt or wrap to be worn around a portion of a human body. In a further feature, the assembly is provided in the form of a belt or wrap to be worn around the midsection of a human.

In another feature, the non-resistive contact sensor assembly further includes a housing that is treated with an ionized liquid.

Broadly defined, the present invention according to another aspect is a non-resistive contact sensor assembly, including: a non-resistive contact sensor device, including a dry electrode component; and an electrostatic shield layer disposed over the sensor device.

In a feature of this aspect, the electrostatic shield layer is a triboelectrically-neutral material.

In another feature of this aspect, the electrostatic shield layer is a electrostatically-shielding material.

In another feature of this aspect, the electrostatic shield layer extends out from the sensor on the surface of the entity being measured or tested.

In another feature of this aspect, the sensor assembly further includes a conducting layer disposed over the electrostatic shield layer. In a further feature, the conducting layer extends out from the outer perimeters of the electrostatic shield layer to the surface of the entity.

In another feature, the non-resistive contact sensor assembly further includes a housing that is treated with an ionized liquid.

Broadly defined, the present invention according to another aspect is a non-resistive contact sensor assembly as shown and described.

Broadly defined, the present invention according to another aspect is a method of reducing movement in a non-resistive contact sensor assembly, as shown and described.

Broadly defined, the present invention according to another aspect is a method of reducing electrostatic interference in a non-resistive contact sensor assembly, as shown and described.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1A:
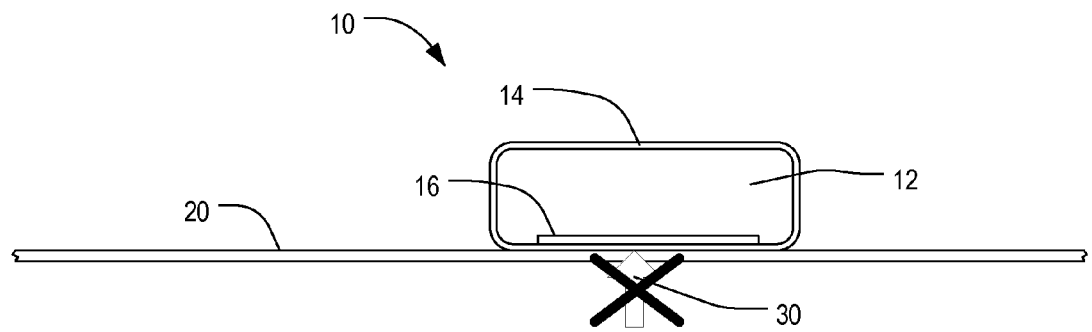
FIG. 1A is a schematic diagram illustrating the use of a non-resistive contact sensor assembly in accordance with a first preferred embodiment of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

The invention relates to methods for attenuating or eliminating unwanted electrostatic interference or "movement" on the signals acquired from non-resistive contact sensors that are utilized for detecting properties of an entity and entities (biological or otherwise). The invention has applicability both for sensors used exclusively and for sensors used in combination with other sensors. For biological entities, the invention utilizes an electric field sensor or sensors, for the measurement of the structural and functional characteristics of organs and other structures, where the electric field sensor does not have resistive contact with the organism, conferring multiple advantages.

More particularly, the invention relates to sensors, sensor housings, fastenings and sensor systems including devices and installations for assemblies for detecting structural and functional signatures associated with electric potentials that may detect a displacement signature within the geomagnetic field, and/or specific components and/or structures that are a component of that entity or entities. Specifically there is no resistive contact between the entity and the signal transduction component of the electric field sensor or sensors. Other sensor types may be added in to provide further information such as for the identification and elimination or attenuation of unwanted electrostatic or movement signal associated with the recording of non-resistive contact electric fields from that entity, in whatever state, such as during active or passive movement.

This invention describes novel methods to mitigate electrostatic and movement interference when using an electric field sensor or sensors that does not have resistive contact with the entity, generally an organism, being monitored. The invention includes combinations and permutations of: using neutral and/or closely matched triboelectric materials to mitigate against the potential for charge (electron) transfer during movement; using conductive materials to dissipate or block charge transfer from the entity or an external source to the non-resistive contact sensor head; using of compressive materials and/or biasing structures to hold the sensor head firmly against the surface of the entity being monitored; using triboelectrically neutral materials (i.e., materials that do not accept or release electrons) to minimize the likelihood for charge transfer to an area where a sensor is; using diodes to transfer charge away from a sensor; and using an ionized liquid to dissipate charge, minimizing static build-up.

FIG. 1A is a schematic diagram illustrating the use of a non-resistive contact sensor assembly 10 in accordance with a first preferred embodiment of the present invention. The sensor assembly 10 includes a sensor device 12 at least partially surrounded by, or embedded in, a cover 14 of anti-triboelectric material. The sensor device 12 includes a dry electrode component 16 that is interior to the cover 14. In some embodiments, the anti-triboelectric material may be a triboelectrically-neutral material, such as cotton. In some embodiments, the anti-triboelectric material may be a material that is triboelectrically matched to the surface 20 of an object to which the sensor is being applied. For example, if the surface is human skin, then the anti-triboelectric material may be leather, which is triboelectrically matched to human skin. The cover 14 is preferably physically bound to the sensor device 12, and in at least some embodiments is physically bound to the dry electrode component 16 portion of the sensor.

Figure 1B:
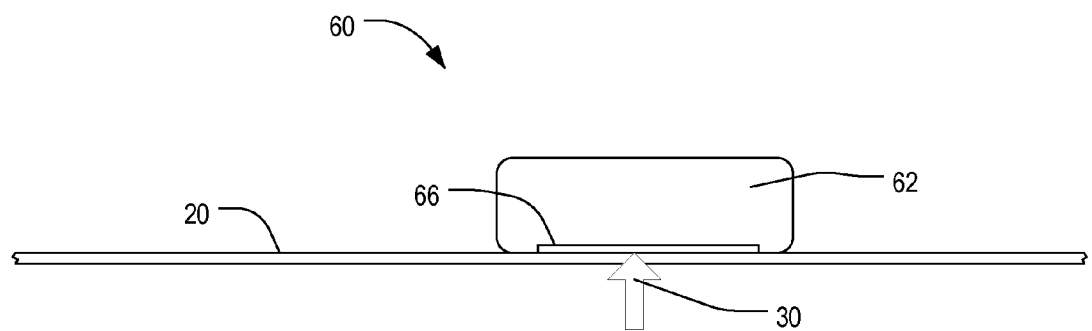
FIG. 1B is a schematic diagram of another non-resistive contact sensor assembly.

As shown in FIG. 1A, when the sensor assembly is placed against the surface 20, the anti-triboelectric material helps prevent (minimizing or even eliminating) contact electrification 30 that would otherwise occur as a result of the triboelectric separation between the dry electrode component 16 and the surface 20 and movement of the dry electrode component 16 against the surface 20. By contrast, FIG. 1B is a schematic diagram of another non-resistive contact sensor assembly 60. This sensor assembly 60 likewise includes a sensor device 62 having a dry electrode component 66, but in the absence of the anti-triboelectric material, contact electrification 30 can and does occur frequently. This, in turn, may cause interference with the target signal acquisition including unwanted noise and/or sensor saturation/railing.

It will be appreciated that in the sensor assembly 10 of FIG. 1A, the cover 14 may utilize a combination of a triboelectrically neutral material with a triboelectrically matched material, and/or may utilize a material having a combination of triboelectrically neutral properties and triboelectrically matching properties. Furthermore, it will be appreciated that the sensor device 12 may be embedded in the cover 14 rather than merely being surrounded by the cover 14.

Figure 2:
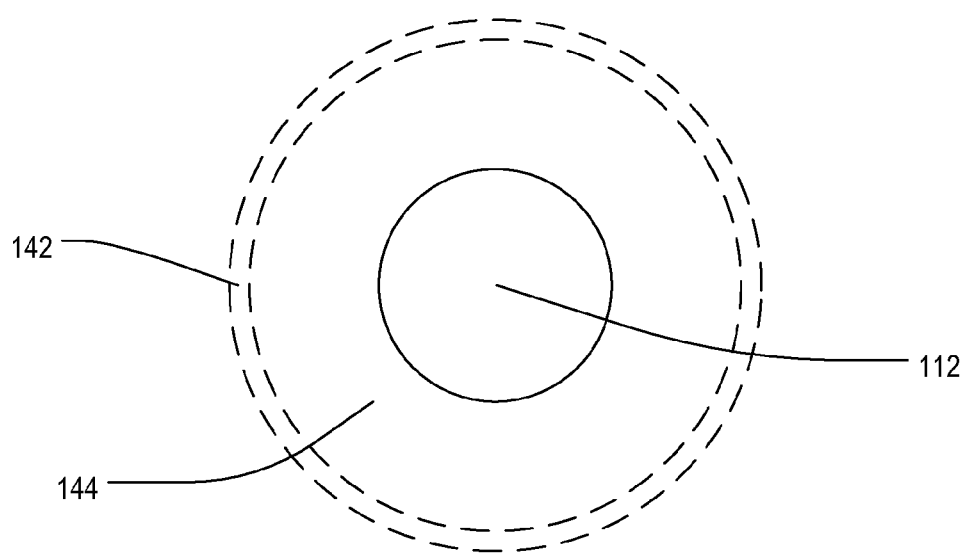
FIG. 2 is a schematic diagram of a non-resistive contact sensor assembly in accordance with another preferred embodiment of the present invention.

FIG. 2 is a schematic diagram of a non-resistive contact sensor assembly 110 in accordance with another preferred embodiment of the present invention. In this sensor assembly, two regions 142,144 surround a sensor device 112, including a dry electrode component (not separately shown). The two regions 142,144 mitigate movement of the sensor electrode relative to the surface of the object being measured, tested, or the like, or create a local area that is relatively protected from the electrostatic build-up and electrical discharge that may otherwise affect sensor performance. An outer region 142 may composed of an elastic or other material that is bound to, or an extension of, a compressive type wearable article, such as a garment, that aids in holding the sensor assembly 110 in place. In various embodiments, the elastic material may include elastane, natural latex, or both. This region may also include a conducting material that aids in dissipation of charge to the surface of the entity, thereby minimizing the chances that the charge will dissipate in a more localized fashion within the area between the outer region 142 the sensor device 112. The outer region 142 could also include a combination of a fastening/elastic/compressive and conductive materials.

In at least some embodiments, an inner region 144 could include a triboelectrically neutral or relatively neutral material, such as but not limited to cotton. One purpose in using such material is to avoid the buildup of electrostatic or other charges, because the material will be at least relatively resistant to, if not able to avoid altogether, accepting or donating electrons. Further, in at least some embodiments, the inner region 144 could include an elastic material, a biasing structure, or both, that acts or act to hold the sensor device 112 in place, thereby minimizing the likelihood of sensor movement against the object surface and leading, in turn, to less chance of contact electrification and movement artifacts. Further, in at least some embodiments, the inner region 144 could include material that is relatively triboelectrically matched to the surface of the object being measured, tested, or the like, thereby minimizing the chances that charge separation will occur when this region 144 and the surface of the object may move together. Further, in at least some embodiments, the inner region 144 could include material that is conductive, allowing for dissipation of any surface or external charge. Finally, it will also be appreciated that the inner region 144 could further be comprised of any combination or permutation of the foregoing types of materials.

Figure 3:
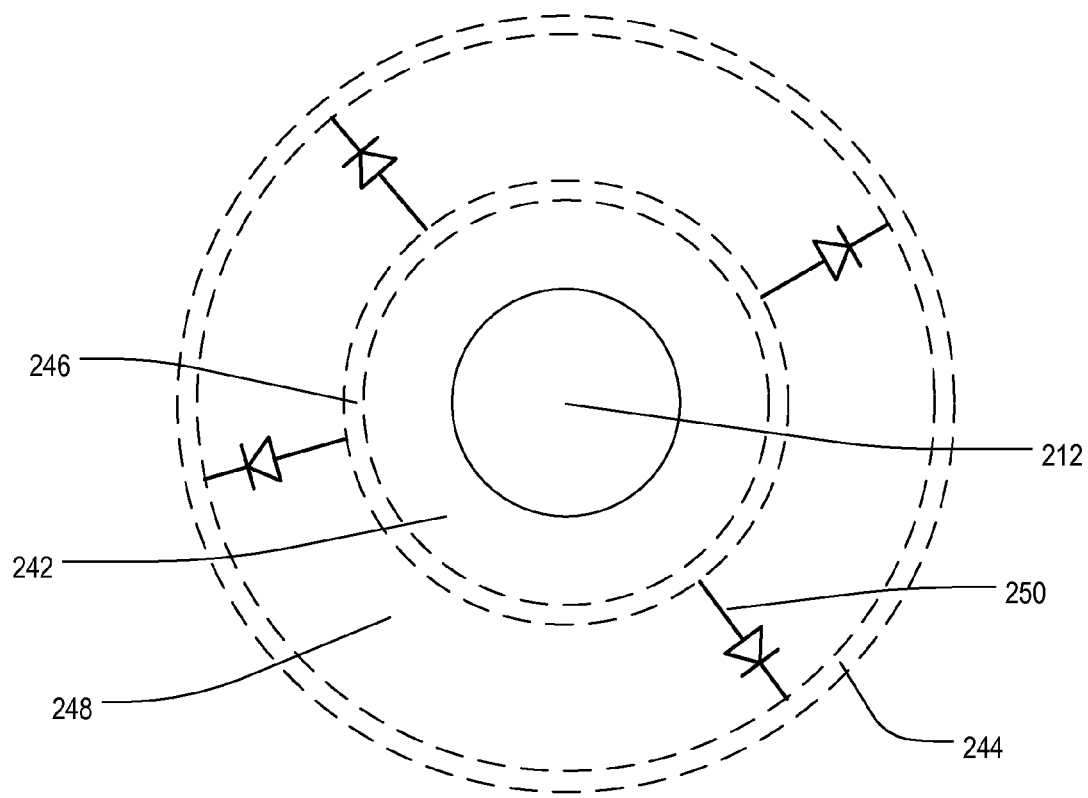
FIG. 3 is a schematic diagram of a non-resistive contact sensor assembly in accordance with another preferred embodiment of the present invention.

FIG. 3 is a schematic diagram of a non-resistive contact sensor assembly 210 in accordance with another preferred embodiment of the present invention. In this sensor assembly 210, diodes 250 may be used for charge transfer away from a sensor device 212. The sensor device 212 is surrounded by, or embedded in, a first inner region 242 where electrical charge is picked up by a boundary region 246 that is comprised at least partly, if not completely, of a conducting material. This charge is then transferred through a second inner region 248, via a diode or network of diodes 250, to an outer region 244.

In various embodiments, each region 242,244,248, other than the boundary region 246, could include a triboelectrically neutral or relatively neutral material, such as but not limited to cotton. One purpose in using such material is to avoid the buildup of electrostatic or other charges, because the material will be at least relatively resistant to, if not able to avoid altogether, accepting or donating electrons. Further, in various embodiments, each region 242,244,248, other than the boundary region 246, could include an elastic material, a biasing structure, or both, that acts or act to hold the sensor device 212 in place, thereby minimizing the likelihood of sensor movement against the object surface and leading, in turn, to less chance of contact electrification and movement artifacts. Further, in various embodiments, each region 242, 244,248, other than the boundary region 246, could include material that is relatively triboelectrically matched to the surface of the object being measured, tested, or the like, thereby minimizing the chances that charge separation will occur when such region 242,244,248 and the surface of the object may move together. Further, in various embodiments, each region 242,244,248, other than the boundary region 246, could include material that is conductive, allowing for dissipation of any surface or external charge. Finally, it will also be appreciated that each region 242,244,248, other than the boundary region 246, could further be comprised of any combination or permutation of the foregoing types of materials.

Figure 4:
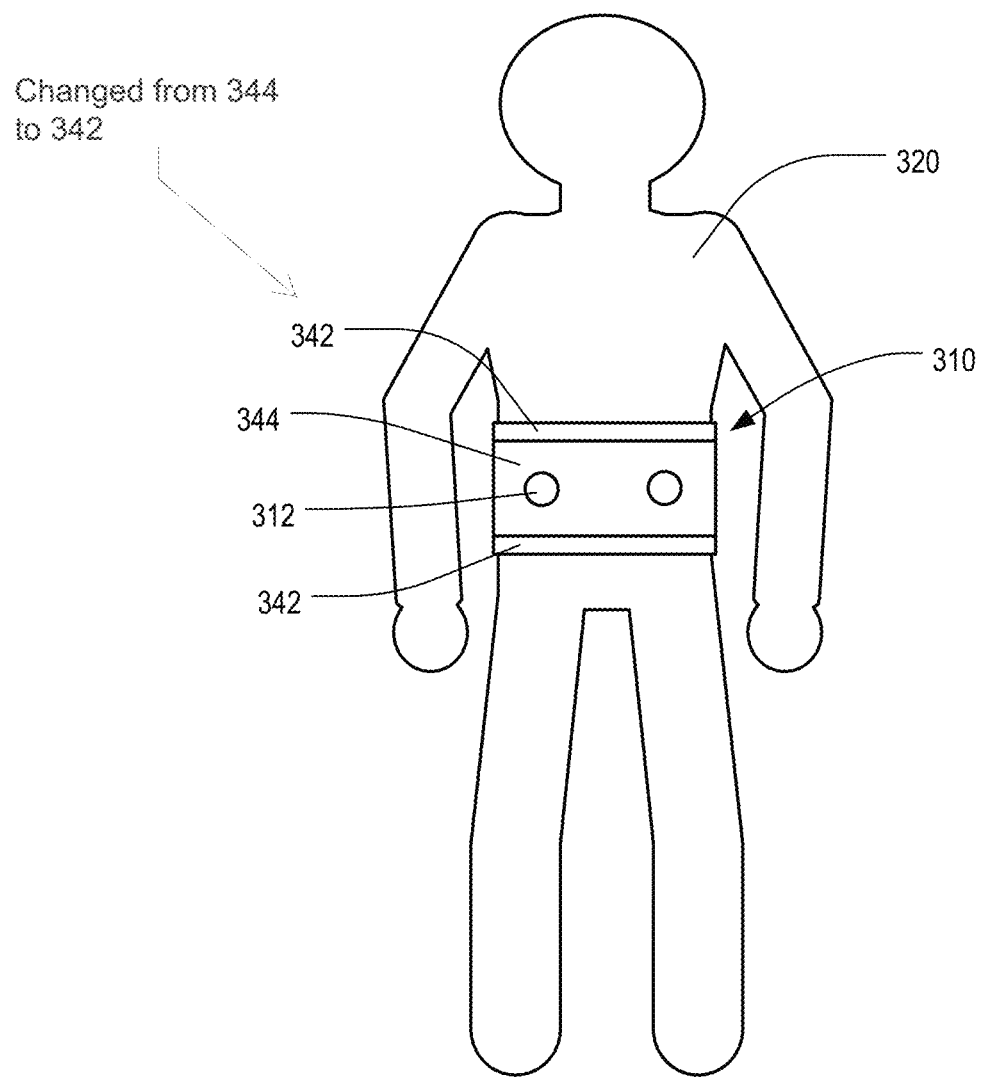
FIG. 4 is a schematic diagram illustrating the use of a non-resistive contact sensor assembly 310 in accordance with another preferred embodiment of the present invention.

FIG. 4 is a schematic diagram illustrating the use of a non-resistive contact sensor assembly 310 in accordance with another preferred embodiment of the present invention. In this sensor assembly 310, the surface region of the entity where a sensor or sensors are housed may be separated from the rest of the surface of the entity using a conducting band. More particularly, one or more sensor devices 312 are surrounded by, or within, a first region 344 that is walled off from the rest of the surface of the entity by a second region 342 that is comprised at least partly, if not completely, of a conducting material. Such a sensor assembly 310 may be provided in a wearable form, such as in the form of a belt or wrap to be worn around the midsection, including thoracic region (chest or upper back) or abdomen, arm, leg, head, or other body portion of a human 320.

In at least some embodiments, the first region 344 could include a triboelectrically neutral or relatively neutral material, such as but not limited to cotton. One purpose in using such material is to avoid the buildup of electrostatic or other charges, because the material will be at least relatively resistant to, if not able to avoid altogether, accepting or donating electrons. Further, in at least some embodiments, the first region 344 could include an elastic material, a biasing structure, or both, that acts or act to hold the sensor device 312 in place, thereby minimizing the likelihood of sensor movement against the object surface and leading, in turn, to less chance of contact electrification and movement artifacts. Further, in at least some embodiments, the first region 344 could include material that is relatively triboelectrically matched to the surface of the object being measured, tested, or the like, thereby minimizing the chances that charge separation will occur when this region 344 and the surface of the object may move together. Further, in at least some embodiments, the first region 344 could include material that is conductive, allowing for dissipation of any surface or external charge. Finally, it will also be appreciated that the first region 344 could further be comprised of any combination or permutation of the foregoing types of materials.

Figure 5:
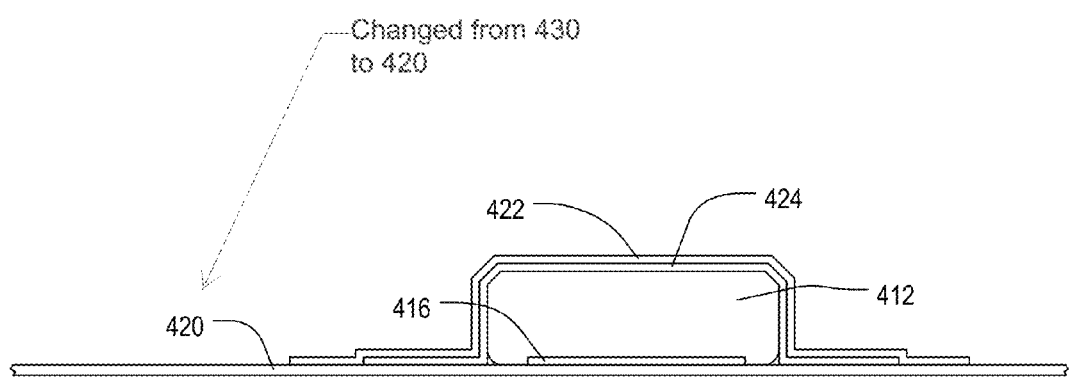
FIG. 5 is a schematic diagram of a non-resistive contact sensor assembly in accordance with another preferred embodiment of the present invention.

FIG. 5 is a schematic diagram of a non-resistive contact sensor assembly 410 in accordance with another preferred embodiment of the present invention. This sensor assembly 410 includes a sensor device 412, having a dry electrode component 416, that has an electrostatic shield layer 424 over it. More particularly, the sensor device 412 has a layer 424 of triboelectrically-neutral or electrostatically-shielding material over it, extending out from the sensor on the surface 420 of the entity being measured, tested, or the like. One material suitable for such a layer 424 is neoprene. In at least some embodiments, one or more additional layer 422 is disposed over the triboelectrically-neutral or electrostatically-shielding layer 424. Such a layer 422 may comprise, in whole or in part, a conducting material for the dispersion of unwanted electrical charge away from the electrode area to the surface of the entity. The conducting layer 422 extends out from the outer perimeters of the triboelectrically-neutral or electrostatically-shielding layer 424 to the surface 420 of the entity. At least one purpose of the conducting layer 422 is to dissipate charge that may occur from external sources, such as moving clothing, away from the sensor electrode 416 and from the surface local to the electrode 416, thereby minimizing the likelihood of sensor drift or saturation.

In at least some embodiments, the conducting layer 422 could include a triboelectrically neutral or relatively neutral material, such as but not limited to cotton. Further, in at least some embodiments, the conducting layer 422 could include an elastic material, a biasing structure, or both, that acts or act to hold the sensor device 412 in place, thereby minimizing the likelihood of sensor movement against the object surface and leading, in turn, to less chance of contact electrification and movement artifacts. Further, in at least some embodiments, the conducting layer 422 could include material that is relatively triboelectrically matched to the surface of the object being measured, tested, or the like, thereby minimizing the chances that charge separation will occur when this layer 422 and the surface of the object may move together. Finally, there may be other layers to shield, hold, or protect the sensor device 412.

In at least some embodiments, including variations of the embodiments described hereinabove, the area being measured, tested, or the like, the sensor housing, and/or clothing worn by a user may be treated with an ionized liquid, such as tap water.

Various advantages may be achieved using one or more of the foregoing embodiments of the present invention. An enhanced signal-to-noise ratio may be achieved for electric field sensors. The effect of electrostatic charge interference with electric field sensors may be minimized or obliterated. The use of electric field sensors during exercise and daily activities may be increased. Usability of electric field sensors with different types of clothing may be improved. The usability of electric field sensors when clothing is moving, such as when it is flapping in the wind, may be improved. The usability of electric field sensors when there is external contact that may knock the sensor may be improved. The usability of electric field sensors may be improved when there is external contact that may result in charge transfer to the entity being measured. The likelihood of contact electrification, sensor DC drift, and sensor saturation may all be decreased.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A non-resistive contact sensor assembly, comprising:
   (a) a non-resistive contact sensor device;
   (b) a first inner region of material in which the sensor device is surrounded or embedded, the first inner region of material comprising a triboelectrically neutral material to minimize contact electrification arising from movement;
   (c) a first boundary region, surrounding the first inner region and comprising a conductive material,
   (d) a second inner region around the boundary region, the second inner region also comprising a triboelectrically neutral to minimize contact electrification arising from movement;
   (e) a second boundary region surrounding the second inner region; and
   (f) at least one diode, disposed in the second inner region and connected between the first boundary region through the second inner region to the second boundary region, the diode arranged to transfer electrostatic charge from the first boundary region to the second boundary region but not from the second boundary region to the first boundary region.

2. The non-resistive contact sensor assembly of claim 1, wherein the second boundary region comprises a conductive material.

3. The non-resistive contact sensor assembly of claim 1, wherein at least one of the first inner region, the second inner region, and the second boundary region includes an elastic material that acts to hold the sensor device in place, thereby minimizing the likelihood of sensor movement against the object surface and leading, in turn, to less chance of contact electrification and movement artifacts.

4. The non-resistive contact sensor assembly of claim 1, wherein at least one of the first inner region, the second inner region, and the second boundary region includes a biasing structure that acts to hold the sensor device in place, thereby minimizing the likelihood of sensor movement against the object surface and leading, in turn, to less chance of contact electrification and movement artifacts.

5. The non-resistive contact sensor assembly of claim 4, wherein the biasing structure includes a spring.

6. The non-resistive contact sensor assembly of claim 1, wherein at least one of the first inner region and the second inner region includes a conductive material.

7. The non-resistive contact sensor assembly of claim 1, wherein the first inner region comprises cotton.

8. The non-resistive contact sensor assembly of claim 7, wherein the second inner region comprises cotton.

9. The non-resistive contact sensor assembly of claim 1, wherein the first inner region comprises leather.

10. The non-resistive contact sensor assembly of claim 9, wherein the second inner region comprises leather.

11. The non-resistive contact sensor assembly of claim 1, further comprising a housing containing the non-resistive contact sensor assembly.

12. The non-resistive contact sensor assembly of claim 1, wherein the at least one diode comprises a network of diodes, each diode arranged to transfer electrostatic charge from the first boundary region to the second boundary region but not from the second boundary region to the first boundary region.

13. A non-resistive contact sensor assembly, comprising:
(a) a non-resistive contact sensor device;
(b) a first inner region of material in which the sensor device is surrounded or embedded, the first inner region of material comprising an anti-triboelectric material to minimize contact electrification arising from movement;
(c) a first boundary region surrounding the first inner region and comprising a conductive material;
(d) a second inner region around the boundary region, the second inner region also comprising an anti-triboelectric material to minimize contact electrification arising from movement;
(e) a second boundary region surrounding the second inner region; and
(f) at least one diode, disposed in the second inner region and connected between the first boundary region through the second inner region to the second boundary region, the diode arranged to transfer electrostatic charge from the first boundary region to the second boundary region but not from the second boundary region to the first boundary region.

14. The non-resistive contact sensor assembly of claim 13, wherein the second boundary region comprises a conductive material.

15. The non-resistive contact sensor assembly of claim 13, wherein at least one of the first inner region, the second inner region, and the second boundary region includes an elastic material that acts to hold the sensor device in place, thereby minimizing the likelihood of sensor movement against the object surface and leading, in turn, to less chance of contact electrification and movement artifacts.

16. The non-resistive contact sensor assembly of claim 13, wherein at least one of the first inner region, the second inner region, and the second boundary region includes a biasing structure that acts to hold the sensor device in place, thereby minimizing the likelihood of sensor movement against the object surface and leading, in turn, to less chance of contact electrification and movement artifacts.

17. The non-resistive contact sensor assembly of claim 16, wherein the biasing structure includes a spring.

18. The non-resistive contact sensor assembly of claim 16, wherein the at least one diode comprises a network of diodes, each diode arranged to transfer electrostatic charge from the first boundary region to the second boundary region but not from the second boundary region to the first boundary region.

19. The non-resistive contact sensor assembly of claim 13, wherein the first inner region and the second inner region includes a conductive material.

20. The non-resistive contact sensor assembly of claim 13, further comprising a housing containing the non-resistive contact sensor assembly.

* * * * *